United States Patent [19]

Balme et al.

[11] 4,113,737
[45] Sep. 12, 1978

[54] POLYAMINES WITH IMIDE GROUPS

[75] Inventors: Maurice Balme, Sainte-foy-les-Lyons; Max Gruffaz, La Mulatiere, both of France

[73] Assignee: Rhone-Poulenc S.A., Paris, France

[21] Appl. No.: 297,738

[22] Filed: Oct. 16, 1972

[30] Foreign Application Priority Data

Oct. 18, 1971 [FR] France .................................. 71.37311

[51] Int. Cl.² .................. C07D 403/10; C07D 403/14
[52] U.S. Cl. ........................... 260/326.26; 260/295 D; 260/302 H; 260/306.8 R; 260/307 G; 548/328; 260/308 R; 260/326.5 FM
[58] Field of Search .................. 260/326.26, 326.5 FM

[56] References Cited

U.S. PATENT DOCUMENTS 3,679,639 7/1972 Bargain .............................. 260/78 U
3,691,195 9/1972 Sambeth et al. ................ 260/326.26

FOREIGN PATENT DOCUMENTS 1,555,564 1/1969 France.

Primary Examiner—Donald G. Daus
Assistant Examiner—M. Berch

Attorney, Agent, or Firm—Stevens, Davis, Miller & Mosher

[57] ABSTRACT

Polyamines possessing imide groups are obtained by heating at least one unsaturated polyimide of the general formula:

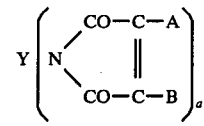

with at least one polyamine of the general formula:

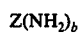

in which $a$ and $b$ each independently represents a number ranging from 2 to 6, Y represents an organic radical of valency $a$ and Z represents an organic radical of valency $b$, in amounts such that the ratio of the number of $NH_2$ groups introduced by the polyamine to the number of imide groups introduced by the polyimide is greater than 1 and at most equal to 5. These polyamines are useful for curing epoxy resins.

13 Claims, No Drawings

POLYAMINES WITH IMIDE GROUPS

The present invention relates to new polyamines with imide groups.

French Pat. No. 1,450,704 discloses di-primary diamines with imide groups joined to one another directly or by an organic radical which does not contain amino groups.

The polyamines of this invention consist essentially of molecules of the general formula:

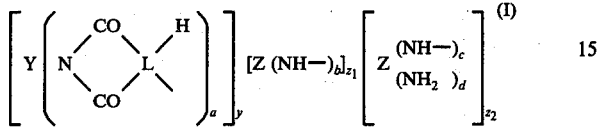

and, optionally, a minor proportion of molecules and/or units of the general formula:

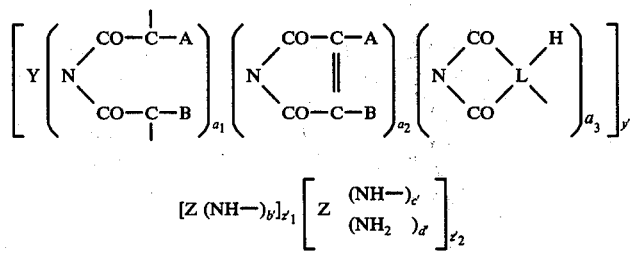

in which formulae the L groups are joined to —NH radicals, $a$ and $b$ each independently represents a number ranging from 2 to 6, $c$ and $d$ each independently represents a number at least equal to 1, with the sum of $c + d$ not exceeding 6, $y$ represents a number ranging from 1 to about 12, $z_1$ represents 0 or a number ranging up to about 11, $z_2$ represents a number ranging up to about 11, $a_1$, $a_2$ and $a_3$ each independently represents 0 or a number such that the sum $(a_1 + a_2 + a_3)$ represents a number from 2 to 6, $y'$ represents 0 or a number from 1 to about 12, $z'_1$ represents 0 or a number ranging up to about 11, $z'_2$ represents 0 if $z'_1$ and $a_3$ are both 0, or represents a number from 1 to about 38, $b'$ represents a number from 2 to 6, $c'$ represents 0 if $y'$ and $z'_1$ are both 0 or represents a number at least equal to 1 if $a_3$ is not 0, $d'$ represents a number at least equal to 1, $c'$ and $d'$ furthermore being such that the sum $(c' + d')$ represents a number from 2 to 6, the various symbols being such that on averge $$ay = bz_1 + cz_2$$

$$a_3y' = b'z'_1 + c'z'_2$$

and the ratio $$\frac{bz_1 + (c + d)z_2 + b'z'_1 + (c' + d')z'_2}{ay + (a_1 + a_2 + a_3)y'} \quad (r)$$

is greater than 1, preferably at least equal to 1.05, but not more than 2,

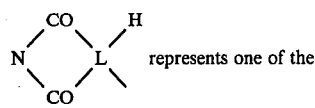 represents one of the radicals of the formulae

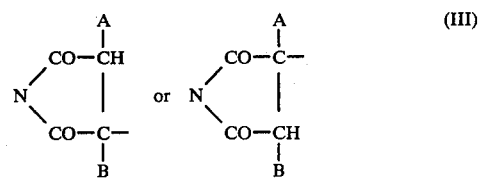

in which each of A and B, which may be identical or different, represents H, CH$_3$ or Cl, Y denotes an organic radical of valency $a$ derived from an unsaturated polyimide of the general formula:

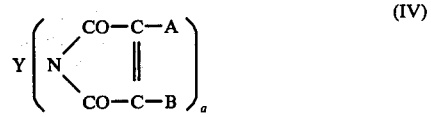

and

Z represents an organic radical of valency $b$ derived from a polyamine of the general formula $$Z(NH_2)_b \quad (V)$$

The symbols Y and Z can, for example, represent a divalent radical such as a straight or branched alkylene radical with less than 13 carbon atoms, a phenylene or cyclohexylene radical or one of the radicals of the formulae:

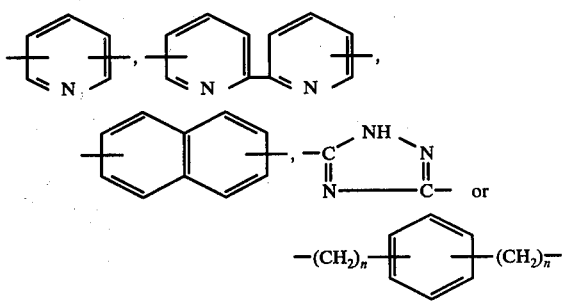

wherein n represents an integer from 1 to 3. The radicals Y and Z can also consist of phenylene or cyclohexylene radicals joined to one another by a simple valency bond or by an inert atom or group such as —O—, —S—, an alkylene group with 1 to 3 carbon atoms,

—CO—,—SO$_2$—,—CONH—,—COO—,—P(O)R$_1$—,

—CONH—X—NHCO—,

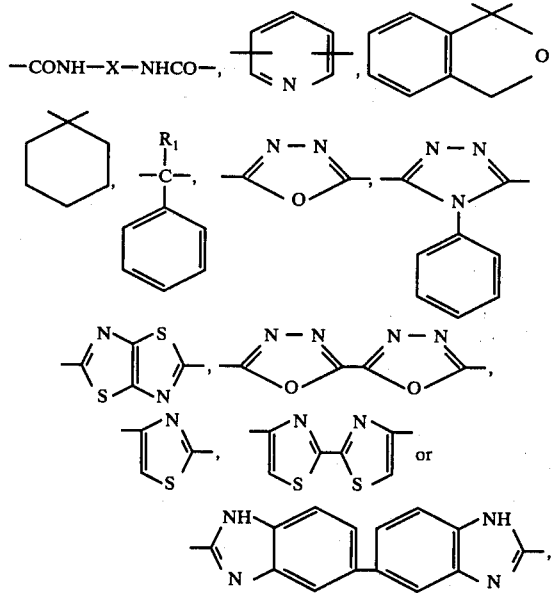

wherein R$_1$ represents a hydrogen atom, an alkyl radical with 1 to 4 carbon atoms, a phenyl radical or a cyclohexyl radical and X represents an alkylene radical with less than 13 carbon atoms. The various phenylene or cyclohexylene radicals, can be substituted by methyl groups. The symbols Y and Z can also represent trivalent to hexavalent radicals, the valencies of which are carried by a benzene ring which is optionally substituted by methyl groups, or by a naphthalene, pyridine or triazine ring; they can also be carried by several benzene rings joined to one another by a simple valency bond or by an inert atom or group which can be one of those described above within the definition of the divalent radicals or can be

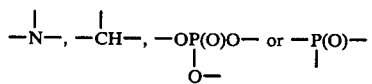

Specific polyimides (IV) include bis-imides such as N,N'-ethylene-bis-maleimide, N,N'-hexamethylene-bis-maleimide, N,N'-meta-phenylene-bis-maleimide, N,N'-para-phenylene-bis-maleimide, N,N'-4,4'-diphenylmethane-bis-maleimide, N,N'-4,4'-diphenylether-bis-maleimide, N,N'-4,4'-diphenylsulphone-bis-maleimide, N,N'-4,4'-dicyclohexylmethane-bis-maleimide, N,N'-4,4'-(3,5-diphenylpyridine)-bis-maleimide, N,N'-pyridinedi-2,6-yl-bis-maleimide, N,N'-α,α'-4,4'-dimethylene-cyclohexane-bis-maleimide, N,N'-meta-xylylene-bis-maleimide, N,N'-para-xylylene-bis-maleimide, N,N'-4,4'-diphenylcyclohexane-bis-maleimide, N,N'-meta-phenylene-bis-dichloromaleimide, N,N'-4,4'-diphenylmethane-bis-citraconimide, N,N'-4,4'-(1,1-diphenyl-propane)-bis-maleimide, N,N'-4,4'-(1,1,1-triphenyl-ethane)-bis-maleimide, N,N'-4,4'-triphenylmethane-bis-maleimide and N,N'-3,5-(1,2,4-triazole)-bis-maleimide. These bis-imides can be prepared using the methods described in, for example, U.S. Pat. No. 3,018,290 and British Patent Specification No. 1,137,592.

The polyimides (IV) can also be the oligomers, with imide groups, of the general formula

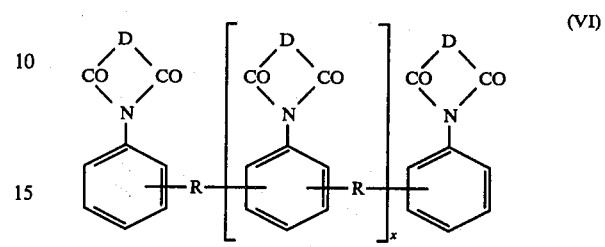

in which x represents a number ranging approximately from 0.1 to 2, in which R represents a divalent hydrocarbon radical with 1 to 8 carbon atoms, derived from an aldehyde or a ketone of the general formula

in which the oxygen atom is joined to a carbon atom of the radical R, D represents a divalent organic radical possessing 2 to 24 carbon atoms, the valencies of which are carried by adjacent carbon atoms, and which is derived from an internal anhydride of the general formula

with at least about 50% of the radicals D representing a radical of the formula

in which A and B are as defined above.

The oligomers with imide groups of formula (VI), can be prepared from an anhydride (VIII), of which 50 mol per cent contain a radical (IX), and an oligomeric polyamine of the general formula

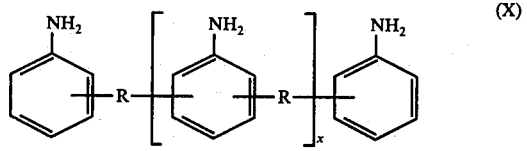

in which R and x are as defined above. The expression "an anhydride of formula (VIII)" is intended to denote one or more anhydrides of the formula:

or several anhydrides of which at least about 50 mol % consist of one or more anhydrides of formula (XI), the remainder consisting of one or more anhydrides of the formula

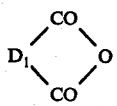 (XII)

in which $D_1$ represents an alkylene, cycloalkylene, aromatic, monocyclic, carbocyclic or heterocyclic radical; typical such anhydrides include the anhydride of succinic, methylsuccinic, dodecylsuccinic, octadecylsuccinic, benzylsuccinic, 1,2-hexahydrophthalic, 1,2-cyclopentanedicarboxylic, 1,2-cyclododecanedicarboxylic, orthophthalic and 1,2-naphthalenedicarboxylic acid. To prepare the oligomers (VI), it is possible to prepare, in a first stage, the corresponding polyamic acids of formula:

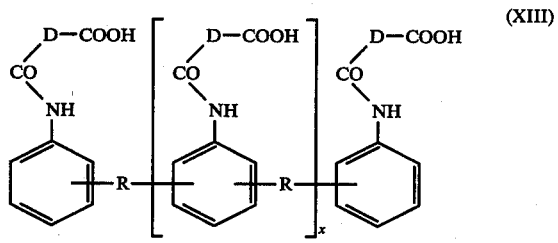 (XIII)

in which formula the various symbols are as defined above, by applying known methods for the preparation of maleamic acids (see, for example, "Maleic Anhydride Derivatives", FLETT and GARDNER). An advantageous process involves bringing the polyamine (X) and the anhydride (VIII) into contact in an organic liquid which is a solvent for the reactants. Suitable solvents which can be used include solvents of high polarity such as dimethylformamide, dimethylacetamide, dimethylsulphoxide, N-methylpyrrolidone and N-methylcaprolactam. It is also possible to use cyclic ethers such as tetrahydrofurane and dioxane; dialkyl ketones such as acetone and diethyl ketone are particularly advantageous. The polyamic acids can thereafter be isolated by filtration. In a second stage, the polyamic acids can be subjected to a cyclising dehydration by applying known methods for the preparation of bis-maleimides from the corresponding bis-maleamic acids. Such methods are described in, for example, U.S. Pat. Nos. 3,018,290, 3,018,292 and 3,127,414. An advantageous process involves carrying out the dehydration with a lower carboxylic acid anhydride, in the presence of a tertiary amine, an organic diluent and a catalyst consisting of a nickel derivative which is soluble in the liquid phase of the reaction mixture; this process can be carried out by applying the method described in French Pat. No. 2,055,969 for the preparation of mono-imides and bis-imides. A particularly advantageous method consists of using directly the suspensions of polyamic acids obtained from the polyamine (X) and the anhydride (VIII) in one of the organic solvents mentioned above. According to a preferred embodiment, the dehydration of the polyamic acids is carried out in acetone with acetic anhydride in an amount from 1.05 to 1.5 mol per molar group of amic acid, in the presence of triethylamine in an amount of the order of 0.15 to 0.5 mol per molar group of amic acid, and of nickel acetate in an amount from 0.5 to 5 mols per molar group of amic acid.

Suitable polyamines (VI) which can be used include the di-primary diamines such as 4,4'-diamino-dicyclohexylmethane, 1,4-diamino-cyclohexane, 2,6-diamino-pyridine, meta-phenylenediamine, para-phenylenediamine, 4,4'-diaminodiphenylmethane, 2,2-bis(4-aminophenyl)-propane, benzidine, 4,4'-diaminophenyl ether, 4,4'-diaminophenyl sulphide, 4,4'-diamino-diphenylsulphone, bis(4-aminophenyl)-methylphosphine oxide, bis(4-aminophenyl)phenylphosphine oxide, N,N-bis(4-aminophenyl)methylamine, 1,5-diaminonaphthalene, -meta-xylylenediamine, para-xylylenediamine, 1,1-bis(para-aminophenyl)phthalane, hexamethylenediamine, 6,6'-diamino-2,2'-dipyridyl, 4,4'-diamino-benzophenone, 4,4'-diamino-azobenzene, bis(4-aminophenyl)phenylmethane, 1,1-bis(4-aminophenyl)-cyclohexane, 1,1-bis(4-amino-3-methylphenyl)-cyclohexane, 2,5-bis(m-aminophenyl)-1,3,4-oxadiazole, 2,5-bis(p-aminophenyl)-1,3,4-oxadiazole, 2,5-bis(m-aminophenyl)-(4,5-d)-thiazolo-thiazole, 5,5'-di(m-aminophenyl)-bis(1,3,4-oxadiazolyl)-(2,2'), 4,4'-bis(p-aminophenyl)-2,2'-dithiazole, m-bis[(4-p-aminophenyl)-thiazolyl-2]benzene, 2,2'-bis(m-aminophenyl)-5,5'-dibenzimidazole, 4,4'-diamino-benzanilide, phenyl 4,4'-diaminobenzoate, N,N'-bis(4-aminobenzoyl)-p-phenylenediamine, 3,5-bis(m-aminophenyl)-4-phenyl-1,2,4-triazole, N,N'-bis(p-aminobenzoyl)-4,4'-diaminodiphenylmethane, bis-p-(4-aminophenylcarbonyl)benzene, bis-p-(4-aminophenoxy)benzene, 3,5-diamino-1,2,4-triazole, 1,1-bis(4-aminophenyl)-1-phenylethane and 3,5-bis(4-aminophenyl)-pyridine.

As examples of polyamines (VI) other than diamines there may be mentioned 1,2,4-triaminobenzene, 1,3,5-triaminobenzene, 2,4,6-triaminotoluene, 2,4,6-triamino-1,3,5-trimethylbenzene, 1,3,7-triamino-naphthalene, 2,4,4'-triaminodiphenyl, 2,4,6-triaminopyridine, 2,4,4'-triaminophenyl ether, 2,4,4'-triaminodiphenylmethane, 2,4,4'-triaminodiphenylsulphone, 2,4,4'-triaminobenzophenone, 2,4,4'-triamino-3-methyl-diphenylmethane, N,N,N,-tri(4-aminophenyl)amine, tri(4-aminophenyl)methane, 4,4',4''-triaminophenyl orthophosphate, tri(4-aminophenyl)phosphine oxide, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diaminobenzidine, 3,3',4,4'-tetraaminophenyl ether, 3,3',4,4'-tetraaminodiphenylmethane, 3,3',4,4'-tetraaminodiphenylsulphone, 3,5-bis(3,4'-diaminophenyl)-pyridine, and the oligomeric polyamines of formula (X); amongst the latter, there may in particular be mentioned those which are formed during the condensation of aniline with an aldehyde or a ketone of formula (VII) such as formaldehyde, acetaldehyde, oenanthaldehyde, benzaldehyde, acetone, methyl ethyl ketine, 2-hexanone, cyclohexanone and acetophenone. The polyamines (X) can be obtained in accordance with known processes, such as those described in French Patents Nos. 1,430,977, 1,481,935 and 1,533,696. The crude mixtures of polyamines obtained in accordance with these processes can be enriched in one or more of their constituents, for example by distillation under reduced pressure.

The preparation of the polyamines with imide groups, of the present invention, can be effected by heating an unsaturated polyimide (IV) and a polyamine (V) in bulk, at a temperature which varies quite considerably depending on the melting point of the reactants but which, as a general rule, is between 50° and 200° C. It is advantageous to homogenise the mixture of the reactants beforehand. A particularly suitable embodiment comprises gradually introducing one of the reactants into the other, which is kept in the liquid state. The preparation of the polyamines with imide groups of this invention can also be effected by heating the reactants in a solvent for at least one of the reactants; such solvents include polar solvents such as dimethylformamide, N-methylpyrrolidone, dimethylacetamide, N-methylcaprolactam, N-acetylpyrrolidone and cresol. It is also possible to use chlorinated hydrocarbons, cyclic ethers and ketones with the proviso that they should remain liquid at the temperature employed, generally between 20° and 150° C. If the reaction product is in the form of a solution, the polyamine with imide groups can be isolated by precipitation with a diluent which is miscible with the solvent employed and does not dissolve the final product; such diluents include water, acetone or a hydrocarbon the boiling point of which does not significantly exceed 120° C, such as heptane or cyclohexane, or a linear ether such as diethyl ether.

It is to be understood that, as used herein, the expression "a polyamine (V)" is intended to cover not only a single polyamine but also mixtures of polyamines of the same functionality, or mixtures of polyamines of which at least two have different functionalities; similar comments apply to the expression "an unsaturated polyimide (IV)".

If $m$ denotes the number of mols of unsaturated polyimide (IV) and $n$ the number of mols of polyamine (V) employed, the ratio $$n\, b/m\, a \qquad \qquad \text{(XIV)}$$

is so chosen that it is greater than 1 and at most equal to about 5 preferably between 1.05 and 2.

The preparation of the polyamines of this invention can be carried out in the presence of a strong acid and/or an inhibitor of free radicals. By "strong acid" is meant, in the Bronsted sense, a monoacid or polyacid, at least one of the ionisation constants (pKa) of which is less than 4.5. Such acids can be inorganic acids such as hydrochloric, sulphuric, nitric and phosphoric acids, optionally substituted by an organic radical, as in, for example, the sulphonic and phosphonic acids. They can also be carboxylic acids; these can be of a simple structure or can possess groups which do not interfere with the reaction between the polyimide (IV) and the polyamine (V). The preferred acid is maleic acid. Generally, from 0.5 to 5% by weight of acid relative to the weight of the polyimide (IV) is employed.

Preferred inhibitors which may be used are hydroquinone, picric acid and diphenyl picrylhydrazine, generally in an amount from 0.01 to 2% by weight of the weight of the polyimide (IV).

the polyamines with imide groups of this invention ae particularly useful for curing epoxy resins. All the customary (1,2-) epoxy resins can be cured in this way including the glycidyl ethers obtained by reaction of epichlorohydrin in known manner with polyols such as glycerol, trimethylolpropane, butanediol or pentaerythritol. Other epoxy resins include the glycidyl ethers of phenols such as 2,2-bis(4-hydroxyphenyl)-propane, bis-(hydroxyphenyl)methane, resorcinol, hydroquinone, pyrocatechol, phloroglucinol, 4,4'-dihydroxydiphenyl and the condensation products of the phenol/aldehyde type. It is also possible to use the reaction products of epichlorohydrin with primary or secondary amines such as bis(4-methylaminophenyl)methane or bis(4-aminophenyl)sulphone, as well as the aliphatic or alicyclic polyepoxides obtained from the epoxidation of the corresponding unsaturated derivatives using peracids. These various types of epoxy resins are extensively described in the literature; as regards their preparation reference may be made to, for example, Houben-Weil, volume 14/2, page 462. The epoxy resins in which the number of epoxy groups in each molecule is at least 2 and preferably greater than 3 are of especial interest; amongst these, essentially aromatic resins are preferred, such as the glycidyl ethers of poly-(hydroxyphenyl)alkanes or of phenol-formaldehyde resins, as well as the resins of the cycloaliphatic type, such as those described in French Patent No. 1,504,104.

In this application, the amount of polyamine with imide groups used can vary within rather wide limits; usually 10% to 95% by weight of polyamine based on the weight of the total mixture (resin + curing agent) is used. These mixtures can be cured at temperatures generally from 150° C to 300° C. In accordance with one embodiment, an intimate mixture of the epoxy resin and of the curing agent is produced. Depending on the physical characterstics of the ingredients, this operation can involve applying the usual techniques for mixing finely divided solids, or of producing a solution or a suspension of one of the constitutents of the mixture in the other, which is kept in the liquid state, if appropriate in a solvent such as dimethylformamide, dimethylacetamide, N-methylpyrrolidone, N-methylcaprolactam, tetrahydrofurane, dioxane, acetone, ethyl acetate, methylene chloride or ethanol. Thereafter the mixture is heated until a liquid or pasty homogeneous mixture is obtained which can be used as such, for example shaped by simple hot casting, and subsequently cured under the abovementioned conditions. It is also possible to use this mixture, after cooling and grinding, in the form of a powder which lends itself to compression moulding operations, optionally in combination with fibrous or pulverulent fillers. This mixture can also be used in solution for the preparation of laminates based on inorganic fibres, vegetable fibres or synthetic fibres.

According to a particular embodiment which is principally advantageous in the case of shaping by casting, the prepolymer is prepared in situ with the epoxy resin by heating the mixture of the epoxy resin with the unsaturated polyimide (IV) and the polyamine (V); a variant of this procedure consists of liquefying the mixture of epoxy resin and unsaturated polyimide (IV) by heating and then adding the polyamine (V) to this liquid mixture.

In the curing of epoxy resins, the polyamine wth imide groups can be combined with one or more monoamines or polyamines previously used as curing agents for epoxy resins. Then it is preferred that the mixture used as the curing agent should contain at least 10% by weight of polyamine with imide groups, or of its precursors.

The following Examples further illustrate the present invention.

EXAMLE 1

(a) 13.9 g of bis(4-aminophenyl)methane are dissolved in 100 cm³ of cresol and thereafter 11.8 g (33mmols) of N,N'4,4'-diphenylmethane-bis-maleimide are gradually added to the solution obtained. The mixture is then heated at 100° C and the gradual disappearance of the NH₂ groups is followed by testing samples of the reaction mixture. After 1 hour 30 minutes, the solution is cooled and then introduced into 500 cm³ of diethyl ether. The precipitate formed is filtered off, washed with diethyl ether and dried under reduced pressure (2mm Hg.) at 50° C overnight.

Finally, 21 g of a powder melting at 190° C and essentially corresponding to the formula:

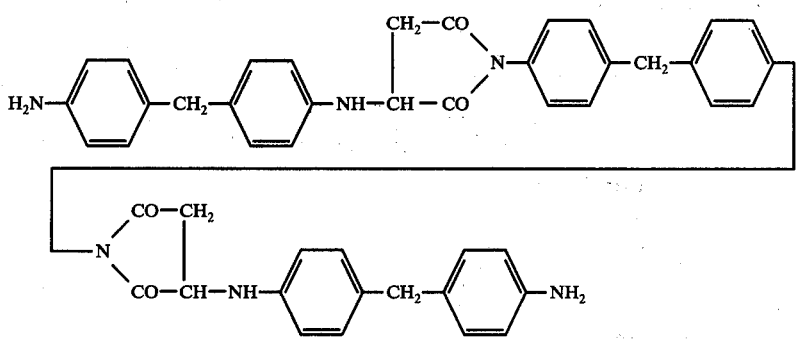

are obtained.

(b) 12.5 g of the powder thus obtained are added to 17.8 g of an epoxy resin previously heated to 120° C, which can be represented by the average formula:

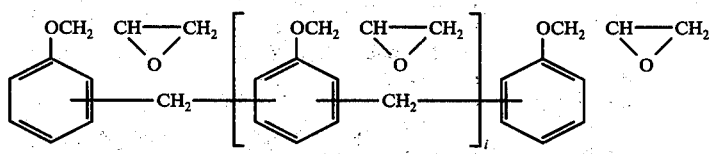

This resin contains, on average, 0.556 epoxy group per 100 g of product.

The solution obtained is degassed under reduced pressure and then cast into a vertical parallelepiped mould preheated to 200° C. The whole is left at this temperature for 1 hour 30 minutes and the article is then released fom the mould after cooling. It is found to have a flexural breaking strength of 14.2 kg/mm² at 25° C.

EXAMPLE 2

18.3 g of N,N'-4,4'-diphenylmethane-bis-maleimide followed by 13.5 g of bis(4-aminophenyl)methane are added to 30.3 g of the epoxy resin described in Example 1 (b) and kept at 130° C. The solution obtained is degassed under reduced pressure and then poured into a vertical parallelepiped mould preheated to 200° C. The whole is kept at this temperataure for 1 hour 30 minutes and then the article is released from the mould after cooling. It is found to have a flexural breaking strength of 12.2 kg/mm² at 25° C.

EXAMPLE 3

The procedure of Example 2 is followed, but using 39.3 g of epoxy resin, 5.6 g of bis-maleimide and 12.5 g of bis(4-aminophenyl)methane.

The moulded article has a flexural breaking strength of 14.3 kg/mm² at 25° C.

EXAMPLE 4

(a) 7.9 g of bis(4-aminophenyl)methane are dissolved in 85 cm³ of cresol and 12.9 g of N,N'-4,4'-diphenylmethane-bis-maleimide, 0.25 g of maleic acid and 0.1 g of hydroquinone are then gradually added to the solution obtained. Thereafter the mixture is heated at 140° C. After 4 hours the solution is cooled and introduced into 200 cm³ of alcohol. The precipitate formed is filtered off, washed with alcohol and dried under reduce pressure (5 mm Hg.) at 60° C overnight.

Finally, 19 g of a polyamine melting at 220° C and containing 0.054 NH₂ group per 10 g of product are obtained. In this polyamine, the ratio of the number of amino groups to the number of imide groups is 1.06.

(b) 20 g of the powder thus obtained are malaxated with 14 g of the epoxy resin described in Example 1 and the mixture is heated at 160° C for 3 minutes. After cooling, the residue obtained is ground and 18 g of powder are taken and introduced into a cylindrical mould (diameter: 7.5 cm). The mould is placed between the platens of a press, previously heated to 220° C, and kept at this temperature for 1 hour under a pressure of 250 bars. After release from the mould whilst hot, and cooling, the article is subjected to a supplementary heat treatment at 250° C for 24 hours. It then is found to have a flexural breaking strength of 13 kg/mm² at 25° C.

EXAMPLE 5

(a) 8.1 g of a polyamine of the average formula:

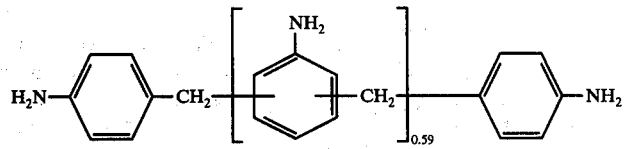

are dissolved in 80 cm³ of cresol and 11.5 g of N,N'-4,4'-diphenyl-ether-bis-maleimide and 0.33 g of maleic acid are then gradually added to the solution obtained. This mixture is subjected to the same treatment as that described in Example 4 (a).

Finally, 17 g of a polyamine melting at 215° C and containing 0.095 NH₂ group per 100 g of product are obtained. In this polyamine, the ratio of the number of amino groups to the number of imide groups is 1.21.

(b) 20 g of the powder thus obtained are malaxated with 18 g of the epoxy resin described in Example 1 and a moulded article is prepared in the manner indicated in Example 4 (b).

The article has a flexural breaking strength of 12 kg/mm² at 25° C.

EXAMPLE 6

(a) 20.2 g of a polyamine of the average formula:

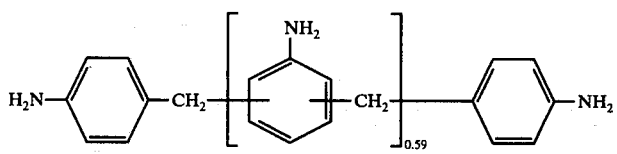

and 32.4 g of N,N'-4,4'-diphenyl-ether-bis-maleimide are introduced into a vessel kept in a liquid heated to 130° C. When the mixture melts, it is stirred and kept under these conditions for 5 minutes. The homogeneous liquid is thereafter poured onto a plate which is placed in an oven at 130° C for 1 hour.

After cooling, the solid obtained is very finely ground. A polyamine melting at 162° C and containing 0.151 NH₂ group per 100 g of product, in which the ratio of the number of amino groups to the number of imide groups is 1.11, is obtained.

(b) A moulded article is prepared, under the conditions described in Example 4 (b), from 20 g of the powder thus obtained and 16 g of the epoxy resin described in Example 1.

The article has a flexural breaking strength of 13 kg/mm² at 25° C.

EXAMPLE 7

(a) 30.3 g of the polyamine described in Example 6 (a) and 32.5 g of an amide of the average formula:

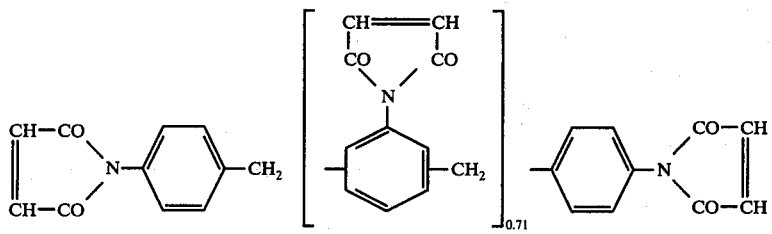

are introduced into a vessel kept in a liquid heated to 130° C.

This mixture is subjected to the same treatment as that indicated above in Example 6 (a). A polyamine melting at 184° C, containing 0.202 NH₂ group per 100 g of product, and in which the ratio of the number of amino groups to the number of imide groups is 1.66, is obtained.

(b) A moulded article is prepared, under the conditions described in Example 4 (b), from 30 g of the powder thus obtained and 30 g of the epoxy resin described in Example 1.

The article has a flexural breaking strength of 11.5 kg/mm² at 25° C.

We claim:
1. A polyamine obtained by heating at least one unsaturated polyimide of the formula:

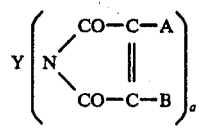

with at least one polyamine of the formula:

$$Z(NH_2)_b$$

in bulk at a temperature sufficient to initiate a reaction, said temperature being between 50° and 200° C., in which $a$ and $b$ each independently represents a number ranging from 2 to 4 corresponding to the valency of Y and Z, respectively, Y and Z, which may be identical or different represents either:

a divalent organic radical which is a straight or branched chain alkylene radical with less than 13 carbon atoms, a phyenylene radical or cyclohexylene radical, a radical of one of the formulae:

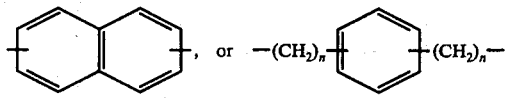

wherein n represents an integer from 1 to 3, or a plurality of phenylene or cyclohexylene radicals joined to one another either by a valency bond or by a group which is one of the following —O—, —S—, an alkylene group with 1 to 3 carbon atoms, —CO—, —SO₂—, —CONH—, —COO—, —P(O)R₁—, —CONH—X—NHCO—,

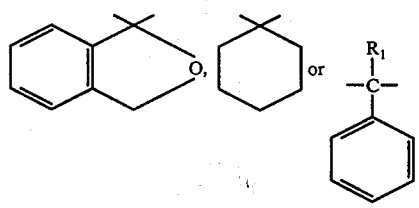

wherein $R_1$ represents a hydrogen atom, an alkyl radical with 1 to 4 carbon atoms, phenyl or cyclohexyl and X represents an alkylene radical with less than 13 carbon atoms, the phenylene or cyclohexylene radical being unsubstituted or substituted by methyl groups; or a 2 to 4 valent radical of formula:

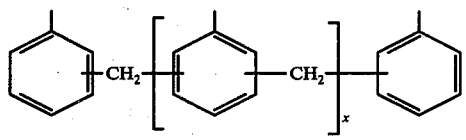

in which $x$ is a number from 0.1 to 2,
A and B, which may be identical or different, represents a hydrogen atom, a methyl group or a chlorine atom,
the ratio of the number of $NH_2$ groups introduced by the polyamine to the number of imide groups introduced by the polyimide being from 1.05 to 2.

2. A polyamine obtained by heating at least one unsaturated polyimide of the formula:

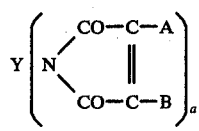

with at least one polyamine of the formula:

in a solvent for the reactants, at a temperature sufficient to initiate a reaction, said temperature being between 20° C. and 150° C., in which $a$ and $b$ each independently represents a number ranging from 2 to 4 corresponding to the valency of Y and Z, respectively, Y and Z, which may be identical or different represents either:
a divalent organic radical which is a straight or branched chain alkylene radical with less than 13 carbon atoms, a phenylene radical or cyclohexylene radical, a radical of one of the formulae:

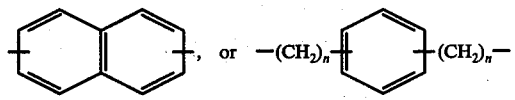

wherein n represents an integer from 1 to 3, or a plurality of phenylene or cyclohexylene radicals joined to one another either by a valency bond or by a group which is one of the following —O—, —S—, an alkylene group with 1 to 3 carbon atoms, —CO—, —$SO_2$—, —CONH—, —COO—, —P(O)$R_1$—, —CONH—X—NHCO—,

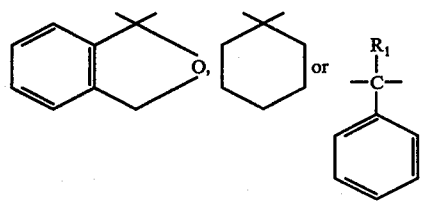

wherein $R_1$ represents a hydrogen atom, an alkyl radical with 1 to 4 carbon atoms, phenyl or cyclohexyl and X represents an alkylene radical with less than 13 carbon atoms, the phenylene or cyclohexylene radical being unsubstituted or substituted by methyl groups; or a 2 to 4 valent radical of formula:

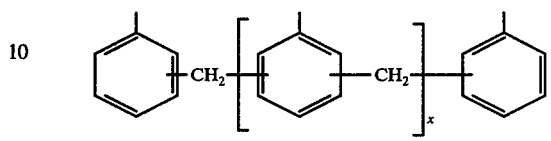

in which $x$ is a number from 0.1 to 2,
A and B, which may be identical or different, represents a hydrogen atom, a methyl group or a chlorine atom,
the ratio of the number of $NH_2$ groups introduced by the polyamine to the number of imide groups introduced by the polyimide being from 1.05 to 2.

3. A polyamine according to claim 1 in which Y and Z, which may be the same or different, each contains 2 to 4 phenylene or cyclohexylene radicals.

4. A polyamine according to claim 2 in which Y and Z, which may be the same or different, each contains 2 to 4 phenylene or cyclohexylene radicals.

5. A polyamine according to claim 1 in which Y and Z, which may be the same or different, represent a radical of the formula:

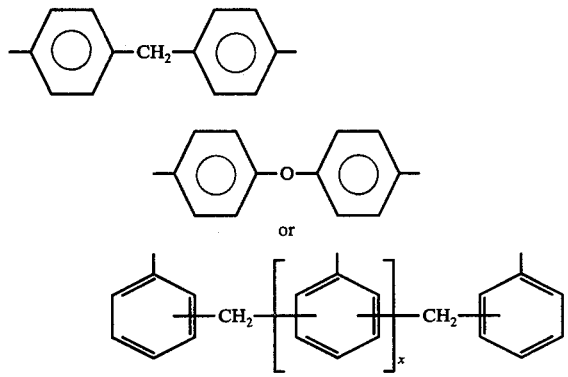

in which $x$ is a number from 0.1 to 2.

6. A polyamine according to claim 2 in which Y and Z, which may be the same or different, represent a radical of the formula:

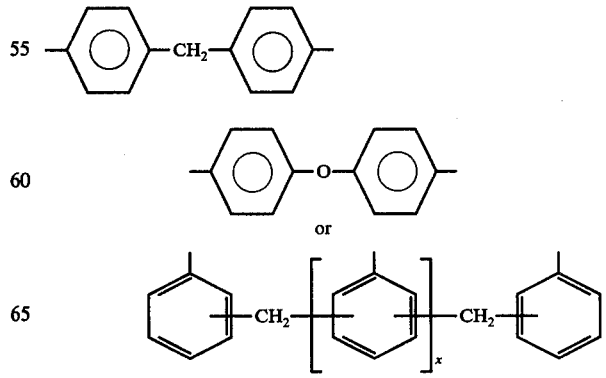

in which x is a number from 0.1 to 2.

7. A polyamine according to claim 1 in which Y and Z, which may be identical or different, represents either: a divalent organic radical which is a straight or branched chain alkylene radical with less than 13 carbon atoms, a phenylene radical or cyclohexylene radical, a radical of one of the formulae:

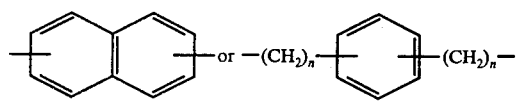

wherein n represents an integer from 1 to 3, or a plurality of phenylene or cyclohexylene radicals joined to one another by a valency bond or by —O—, —S—, or an alkylene group with 1 to 3 carbon atoms.

8. A polyamine according to claim 2 in which Y and Z, which may be identical or different, represents either: a divalent organic radical whic is a straight or branched chain alkylene radical with less than 13 carbon atoms, a phenylene radical or cyclohexylene radical, a radical of one of the formulae:

wherein n represents an integer from 1 to 3, or a plurality of phenylene or cyclohexylene radicals joined to one another by a valency bond or by —O—, —S—, or an alkylene group with 1 to 3 carbon atoms.

9. A polyamine according to claim 2 in which the solvent is dimethylformamide, N-methylpyrrolidone, dimethylacetamide, N-methylcaprolactam, N-acetylpyrrolidone or cresol.

10. A polyamine according to claim 1 in which Y or Z represents a radical or formula:

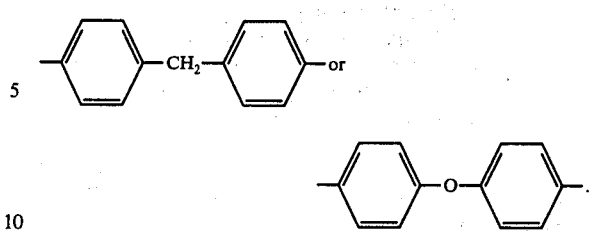

11. A polyamine according to claim 2 in which Y or Z represents a radical of formula:

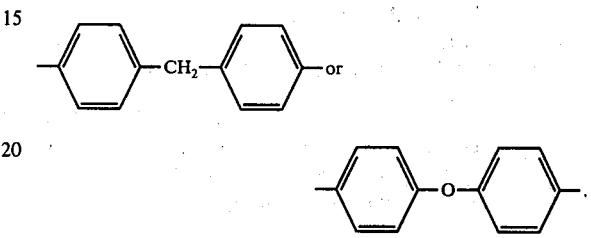

12. A polyamine according to claim 1 in which the polyamine has the general formula:

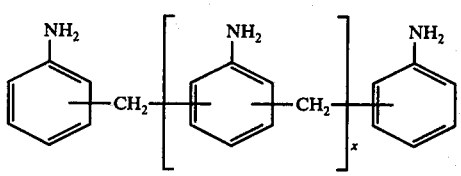

in which x is a number from 0.1 to 2.

13. A polyamine according to claim 1 in which the polyamine has the general formula:

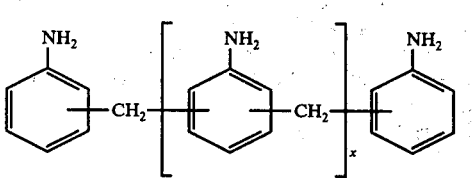

in which x is a number from 0.1 to 2.

* * * * *